(12) United States Patent
Abe et al.

(10) Patent No.: US 7,955,472 B2
(45) Date of Patent: *Jun. 7, 2011

(54) INTERIOR CONSTRUCTION MATERIAL HAVING DEODORIZING ACTIVITY

(75) Inventors: Yoshinobu Abe, Tokushima (JP); Michio Nishi, Tokyo (JP); Itaru Yokoyama, Tokyo (JP)

(73) Assignees: Otsuka Kagaku Kabushiki Kaisya, Osaka-shi (JP); Yoshino Gypsum Co., Ltd., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/543,689

(22) Filed: Aug. 19, 2009

(65) Prior Publication Data

US 2010/0047623 A1 Feb. 25, 2010

Related U.S. Application Data

(62) Division of application No. 10/398,539, filed as application No. PCT/JP01/08854 on Oct. 9, 2001, now Pat. No. 7,604,853.

(30) Foreign Application Priority Data

Oct. 10, 2000 (JP) ................................ 2000-308723
Jun. 6, 2001 (JP) ................................ 2001-171036

(51) Int. Cl.
*D21H 13/44* (2006.01)
*B32B 13/00* (2006.01)
(52) U.S. Cl. ....................................... 162/161; 428/703
(58) Field of Classification Search .................. None
See application file for complete search history.

(56) References Cited

U.S. PATENT DOCUMENTS

| 3,410,813 A | 11/1968 | Campbell et al. |
| 3,878,278 A | 4/1975 | Miller et al. |
| 3,965,051 A | 6/1976 | Markusch et al. |
| 4,857,364 A | 8/1989 | Von Bonin |
| 5,015,334 A | 5/1991 | Derrick |
| 5,215,827 A | 6/1993 | Dotzauer et al. |
| 5,571,379 A | 11/1996 | Derrick |
| 5,644,880 A | 7/1997 | Lehnert et al. |
| 6,077,794 A | 6/2000 | Tabata et al. |
| 6,586,066 B1 | 7/2003 | Buckwalter et al. |

FOREIGN PATENT DOCUMENTS

| JP | 51-111825 A | 10/1976 |
| JP | 7-061889 B | 7/1995 |
| JP | 9-207298 A | 8/1997 |
| JP | 2686792 B2 | 12/1997 |
| JP | 2739872 B2 | 4/1998 |
| JP | 10-212809 A | 8/1998 |

(Continued)

OTHER PUBLICATIONS

USPTO Office Action mailed Mar. 3, 2006 for Parent U.S. Appl. No. 10/398,539.

(Continued)

*Primary Examiner* — Gordon R Baldwin
(74) *Attorney, Agent, or Firm* — Ladas & Parry LLP

(57) ABSTRACT

High odor eliminating property is provided to a building material for interiors by compounding a hydrazide compound. Additionally, the odor eliminating property of the building material for interiors is improved and hygroscopicity and size stability at the time of use are provided by adding and compounding an organic carbide, an inorganic hygroscopic material, and a water repellent. Also, an interior structure in which these building materials for interiors are employed is provided.

1 Claim, 3 Drawing Sheets

FOREIGN PATENT DOCUMENTS

| | | |
|---|---|---|
| JP | 10-226962 A | 8/1998 |
| JP | 11-020109 A | 1/1999 |
| JP | 11-048214 A | 2/1999 |
| JP | 11-058594 A | 3/1999 |
| JP | 11-303303 A | 11/1999 |
| JP | 2000-006730 A | 1/2000 |
| JP | 2000-095980 A | 4/2000 |
| JP | 2000-107275 A | 4/2000 |
| JP | 2000-144016 A | 5/2000 |
| JP | 2000-152979 A | 6/2000 |
| JP | 2000-273231 A | 10/2000 |
| JP | 2001-089217 A | 4/2001 |
| JP | 2001-187402 A | 7/2001 |
| JP | 2001-323637 A | 11/2001 |

OTHER PUBLICATIONS

USPTO Office Action mailed Jan. 23, 2008 for Parent U.S. Appl. No. 10/398,539.

USPTO Office Action mailed Dec. 24, 2008 for Parent U.S. Appl. No. 10/398,539.

INTERIOR CONSTRUCTION MATERIAL HAVING DEODORIZING ACTIVITY

TECHNICAL FIELD

The present invention relates to a building material excellent in odor eliminating property, and an interior structure of a building having an odor eliminating property using the same.

BACKGROUND ART

Recently in the housing industry, while cost reduction has been advanced by streamlining construction techniques and increasing efficiency of construction techniques, the attainment of high performance and stabilization of quality of building materials has been intended, and design and building construction have been increased so that airtight and thermal insulation properties of indoor space are improved from the viewpoint of energy-saving.

In addition to that, contamination of indoor air with a VOC (volatile organic compound) and the resulting damage to health of residents have been problems known as so-called "chemical anaphylaxis" or "sick-house syndrome". For example, toluene and xylene as solvents for paint, and para-dichlorobenzene contained in an aromatic substance other than formaldehyde generated from building materials such as plywood or generated from an adhesive used for assembling furniture at the time of applying these building materials, and acetaldehyde originating from inside smoking, are known to cause various constitutional symptoms such as, for example, dyspnea, vertigo, vomiturition, spasmus, rigor, and shock, and harmful effects such as depression and lowering in visual acuity to a human body.

Against that, "Health Housing Study Group" involving three ministries and an agency of the Japanese government, namely, the Ministry of Construction, the Ministry of Health and Welfare, the Ministry of International Trade and Industry, and the Forestry Agency, as well as academic experts and related economic organizations was started in 1996. Research and studies on the problem of contamination of indoor air have been advanced, and specific directions have been proposed. Recently, the Ministry of Health and Welfare proposed 400 $\mu g/m^3$ for existing housing and 1000 $\mu g/m^3$ for new residential housing as a provisional goal for the total amount of organic compounds (referred to as TVOC below) contained in indoor air of housing, to the Sick House Problem Study Group of the ministry, which is currently being discussed. Additionally, in Housing and Urban Development Corporation, such measure has been taken from 1997 that adhesive used for wallpaper is changed to of a non-formaldehyde generating type.

In such a situation, as a measure for preventing contamination of indoor air, for example, employing an adhesive containing no formaldehyde and reducing by ventilation the concentration of contamination in indoors have been proposed.

However, a formaldehyde-based adhesive has prevailed as an adhesive used particularly for bonding plywood. This kind of adhesive is very inexpensive and an adhesive that is extremely excellent in adhesive strength apart from a disadvantage such that problematic formaldehyde is released by the adhesive. Although various alternatives have been developed by each adhesive maker, an effective alternative to the formaldehyde-based adhesive has not been found yet. For example, a problem is that an adhesive containing no formaldehyde as excellent as a formaldehyde-based adhesive is necessarily expensive and not economical. Additionally, in the case of ventilation, although it is effective to dilute the VOC, it is not a fundamental solution in respect to being no better than a measure after generation and it has a problem in energy-saving since it is required to exchange indoor air with outdoor air constantly.

Also, in the housing industry, a concern is directed to instantaneously capturing a VOC such as formaldehyde generated from not only a building material for interiors used for forming residential rooms by plywood, but also a building material such as plywood and an adhesive used for a structure between an exterior material and an interior material, inside a partitioning wall structure, above a ceiling, under a floor, and further for furnishing goods such as furniture.

For example, various attempts have been made to provide the function of capturing a VOC and eliminating odor to a gypsum-based building material, particularly a gypsum board, which is excellent in thermal insulation property and economy and widely used as for a base material for interiors having air permeability to some extent. For example, in Japanese Laid-open Patent application No. 9-207298, it is proposed to compound an amino-compound or a urea into a base paper for gypsum board constituting a surface of a gypsum board with the aim of capturing formaldehyde, and in Japanese Laid-open Patent application No. 11-303303, it is proposed to compound silica gel and catechin into a gypsum board so as to provide odor eliminating and anti-bacterial properties. Furthermore, in Japanese Laid-open Patent application No. 11-20109, it is proposed to provide an odor eliminating effect by employing a decoration sheet having a formaldehyde-capturing layer in a gypsum board, in which layer an organic amino compound is employed.

However, the above-mentioned propositions in regard to a gypsum board are aimed at only an odor eliminating effect for aldehydes such as formaldehyde originating from a building material such as plywood and furniture and acetaldehyde arising from smoking and the amount of capturing has a limitation when an odor eliminating effect for a VOC such as formaldehyde contained in an adhesive used at the time of assembling a building material is considered.

DISCLOSURE OF THE INVENTION

Accordingly, it is an object of the present invention is to provide a building material for interiors, excellent in convenience, thermal insulation property, economy, as well as hygroscopicity and size stability at the time of use, and having an excellent odor eliminating property so that the VOC as described above is captured and not released, which VOC is generated even when a formaldehyde-based adhesive is employed for assembling a building material such as plywood and furniture and originating from other factors, taking the above-mentioned situation into account. Also, it is an object of the present invention to provide an interior structure of a building that can reduce the concentration of indoor contamination without indoor ventilation regardless of whether the building is a new construction building or a used building.

The above objects are achieved by the following present invention. That is, the present invention provides a building material for interiors having an odor eliminating property characterized in that at least one hydrazide compound is compounded.

Also, the present invention provides an interior structure of a building characterized by containing the building material for interiors as claimed in any one of claims 1 through 14.

Furthermore, the present invention provides a method of modifying an interior structure of a building characterized in that the building material for interiors as claimed in any one of claims 1 through 14 is applied on a surface of an existing building so as to modify.

As a result of an active investigation in order to solve the problems of the prior art described above, the inventors of the present invention have found that by compounding at least one hydrazide compound having a property of capturing aldehydes into a building material for interiors, the excellent aldehydes capturing property of the material is exhibited for the building material, and by compounding an organic carbide, a VOC other than aldehydes can be also effectively captured.

Additionally, it has been found to obtain an odor eliminating property improved in respect to the property of capturing a VOC as well as excellent hygroscopicity and size stability without canceling out one another's properties and further not to release the captured VOC even in a severe condition of temperature elevation, as the hydrazide compound is used in combination with one or more materials in an organic carbide, an inorganic hygroscopic material, and a water repellent, and the present invention is achieved.

Furthermore, other objects and features of the present invention will be apparent from the following description that is illustrated in conjunction with the drawings.

BEST MODE FOR CARRYING OUT THE INVENTION

Figure 1:
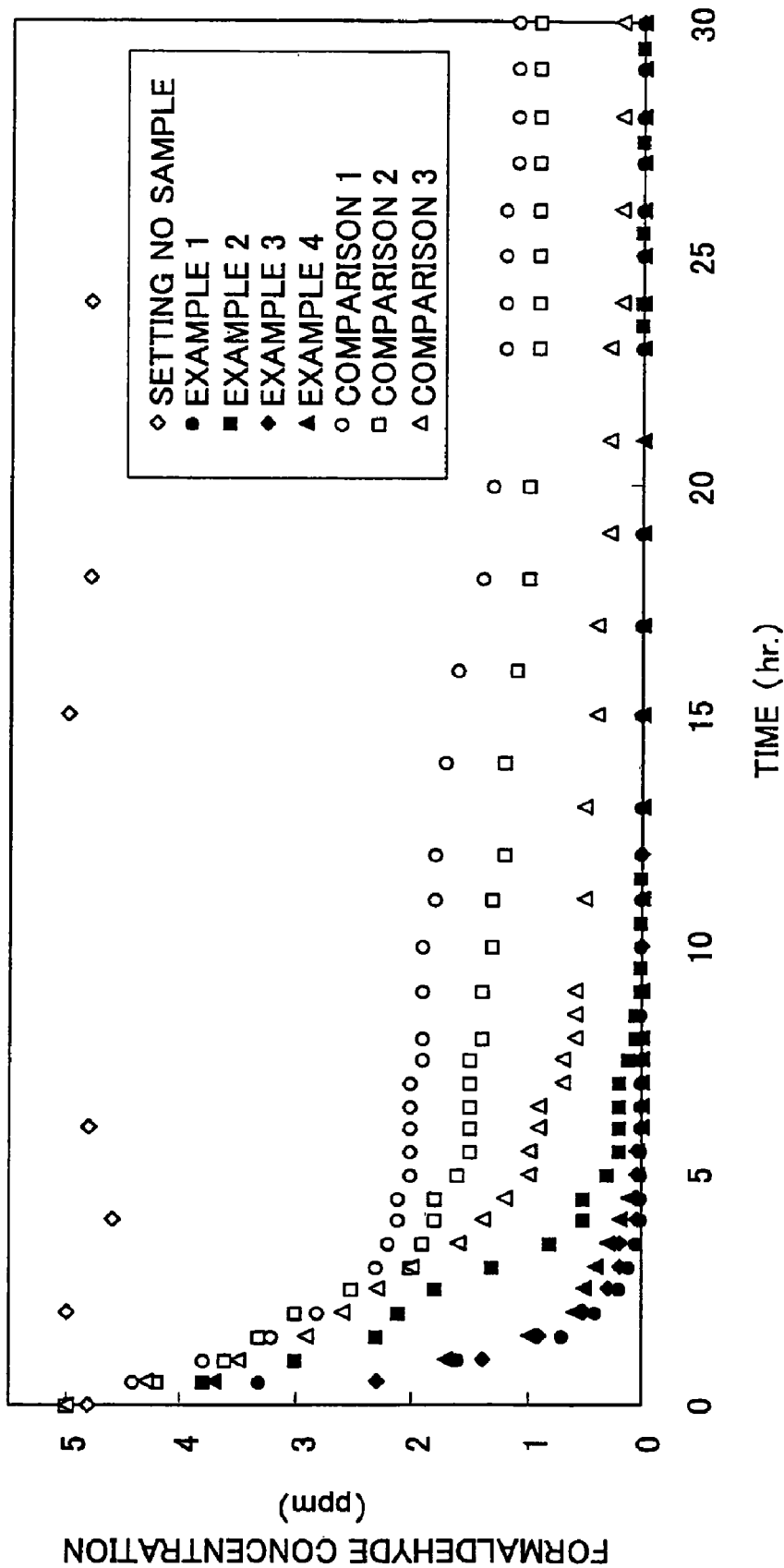
FIG. 1 is a graph of plotting the results of a test of an odor eliminating property against formaldehyde gas.

The present invention will be further illustrated in detail with reference to embodiments of the invention.

As a building material for interiors according to the present invention, a powder-type or pasty building material that is formulated with the aim for applying (coating) or spraying by using a method of adding water and mixing in a factory, a construction site, or a modification construction site can be shown as an example, other than a building material of which a base material is an inorganic material, for example, gypsum or cement, that is made be a board-shaped by using means such as water addition molding, sheet-making molding, extrusion molding, mold molding, and compression molding.

For example, in the case of a gypsum-based building material of which a base material is gypsum, as a board-shaped one, a gypsum board formed by coating a plaster core with a base paper for gypsum board (JIS A 6901), a perforated gypsum board for sound absorption (JIS A 6301), a wood wool gypsum board, a fiber reinforced gypsum board, and a glass fiber cloth-containing gypsum board can be provided.

Herein, the glass fiber cloth-containing gypsum board is a building board including a core material being gypsum and a fiber non-woven fabric such as a glass fiber non-woven fabric buried over at least one surface thereof, in which the densities of gypsum layers being surface layers contacting with both surfaces of the non-woven fabric, respectively, and a gypsum layer constituting a core layer can be easily controlled and the surface hardness can be improved, and board-shaped ones with a wide variety of board-thicknesses can be obtained.

Additionally, an admixture such as a glass fiber and an organic fiber can be compounded into the gypsum core constituting the building board.

Also, as a gypsum-based building material of which a base material is powder-type gypsum, a gypsum plaster (JIS A 6904), a gypsum-based adhesive, a gypsum-based self-leveling floor covering material, gypsum-based putties, and a gypsum-based jointing material can be shown as examples. Then, as for gypsum-based putties and the gypsum-based jointing material, there is a pasty one kneaded so as to be able to be used immediately.

Additionally, the gypsum is roughly classified into three modifications, i.e., dihydrate gypsum, semihydrate gypsum, and anhydrous gypsum. Publicly known β-type semihydrate gypsum, α-type semihydrate gypsum, or a semihydrate gypsum of a mixture thereof provided by calcining a chemical gypsum represented by a natural gypsum, a phosphogypsum and a desulfurized gypsum independently or in combination is employed as a main material for a powder-type building material for interiors. Also, a core material of a building material for interiors, of which the shape is board-shaped, is obtained by employing the semihydrate gypsum as a main material, adding water thereto and kneading, molding, and subsequently hardening, and a gypsum before calcining, so-called dihydrate gypsum is used for a kneaded building material to be able to be used immediately.

Also, as a board-shaped building material of which a base material is cement, there are a wood wool cement board (JIS A 5426), a pulp cement board (JIS A 5414), an ALC panel (JIS 5416), a fiber reinforced cement board (JIS A 5430), and a slate (JIS A 5102). As a powder-type building material, there are various kinds of cements such as Portland cement, alumina cement, and Portland blast furnace cement.

Furthermore, a board-shaped, powder-type, or pasty building material of which a base material is lime, dolomite, an inorganic carbonate, or a mineral of an inorganic silicate may be provided.

As for a hydrazide compound employed in the present invention, provided are a compound having at least one hydrazide group in the molecule, i.e., a monohydrazide compound having one hyrazide group in the molecule, a dihydrazide compound having two hydrazide groups in the molecule, and a polyhidrazide compound having equal to or more than three hydrazide groups in the molecule.

As an embodiment of the monohydrazide compound, for example, a compound represented by the general formula:

$$R\text{—}CO\text{—}NHNH_2 \qquad (1)$$

can be provided, wherein R represents a hydrogen atom, an alkyl group, or an aryl group which may have one or more substituents.

In the general formula (1), as the alkyl group represented by R, for example, a straight chain alkyl group in which the number of carbons is 1 through 12, such as a methyl group, an ethyl group, a n-propyl group, a n-butyl group, a n-pentyl group, a n-hexyl group, a n-heptyl group, a n-octyl group, a n-nonyl group, a n-decyl group, and a n-undecyl group can be provided.

As the aryl group, for example, a phenyl group, a biphenyl group, and a naphtyl group can be provided, and the phenyl group is preferred among these. Also, as a substituent for the aryl group, for example, a hydroxyl group, a halogen atom such as fluorine, chlorine, and bromine, and a straight or branched chain alkyl group in which the number of carbons is 1 through 4, such as a methyl group, an ethyl group, a n-propyl group, an iso-propyl group, a n-butyl group, a tert-butyl group, and an iso-butyl group can be provided.

More specifically, as the hydrazide compound represented by the general formula (1), dodecanohydrazide, salicylohydrazide, formohydrazide, acetohydrazide, propionohydrazide, p-hydroxybenzohydrazide, naphtohydrazide, and 3-hydroxy-2-naphtohydrazide can be shown as examples.

As an embodiment of a dihydrazide compound, for example, a compound represented by the general formula:

$$H_2NHN—X—NHNH_2 \qquad (2).$$

can be provided, wherein X represents a group —CO— or a group —CO-A-CO—, and A represents an alkylene group or an arylene group, which may have one or more substituents.

In the general formula (2), as the alkylene group represented by A, for example, a straight chain alkylene group in which the number of carbons is 1 through 12, such as a methylene group, an ethylene group, a trimethylene group, a tetramethylene group, a pentamethylene group, a hexamethylene group, a heptamethylene group, an octamethylene group, a nonamethylene group, a decamethylene group, and an undecamethylene group can be provided. As a substituent for the alkylene group, for example, a hydroxyl group can be provided.

As the arylene group, for example, a phenylene group, a biphenylene group, a naphtylene group, an anthrylene group, and a phenanthrylene group can be provided and the phenylene group and the naphtylene group are preferred among these. As a substituent for the arylene group, the same ones as the substituents for the aryl group can be provided.

As the dihydrazide compound represented by the general formula (2), specifically, for example, provided is a dihydrazide derived from a dibasic acid, such as oxalodihydrazide, malonodihydrazide, succinodihydrazide, adipodihydrazide, azelodihydrazide, sebacodihidrazide, dodecanedicarbodihydrazide, maleodihydrazide, fumarodihydrazide, diglycolodihydrazide, tartarodihydrazide, malodihidrazide, isophthalodihydrazide, terephthalodihydrazide, a dihydrazide derived from a dimer of carboxylic acids, and 2,5-haphthodihydrazide. Furthermore, each kind of dihydrazide derived from a dibasic acid disclosed in Japanese Examined Application publication No. 2-4607 or 2,4-dihydtazino-6-methylamino-1,3,5-triazine can also be employed as a hydrazide for the present invention.

As for a polyhydrazide compound, specifically, polyacrylohydrazide can be shown as an example.

Among the dihydrazide compounds, a dihydrazide compound is preferred as a compounded material for the present invention, and a dihydrazide derived from a dibasic acid is particularly preferred.

A method of compounding the hydrazide into a building material for interiors according to the present invention is not limited. Addition into the base material may be made in powder-form, water-based slurry-form, or aqueous solution-form and use may be made of the previously mentioned mixing and kneading of an admixture to be contained in the building material for interiors mentioned below. Furthermore, a coating to the admixture may be provided so as to make an addition into the base material. Also, the compounds may be impregnated into a board-shaped or putty-formed building material for interiors. Moreover, if the building material for interiors is a gypsum board, at the time of sheet-making of a base paper being a surface material for the gypsum board, the compound in a water-based slurry form may be added to defibrated pulp fibers.

Additionally, one or more kinds of the hydrazides can be compounded into a building material for interiors in the present invention.

The loading of the hydrazide compound is 0.01 through 10 parts by weight, preferably 0.01 through 5 parts by weight, and more preferably 0.01 through 1 parts by weight per 100 parts by weight of a base material. The more the loading of the hydrazide compound to the building material for interiors is increased, the more the odor eliminating property can be improved; however, preference is not provided since the compound is very expensive and inferior in respect to economy. On the other hand, in the case of the loading less than 0.01 parts by weight, the loading is too small to exhibit a significant odor elimination effect.

Also, one or more kinds of an organic carbide, an inorganic hygroscopic material and a water repellent can be compounded into the building material for interiors having an odor eliminating property according to the present invention, with the aim of effectively capturing other VOCs which are not able to be captured by the hydrazide compounds as well as with the aim of improving the hygroscopicity and the size stability. Next, these materials are explained.

As an organic carbide is used in the building material for interiors according to the present invention, one or more kinds of carbides selected from all that are classified by a production district, a carbonization method, the degree of carbonization proceeding, and a raw material as well as white coal, black coal, vegetable coal carbonized at low temperature, charcoal made from bamboo, charcoal made from compression molded sawdust, and activated charcoal that is carbonized and activated can be used. In general, it in known that charcoals such as vegetable coal and activated charcoal in which carbonization is made at the carbonization temperature of approximately 600 through 700° C. exhibit the best adsorption property, and those having such an excellent adsorption property can be preferably used. Additionally, from the view point of zero-emission in recent years, carbides from thinned wood in forests, drift wood, weeds, tea-leaves, coffee-grounds, vegetable debris, vegetable and nut grounds, left-over meals, paper, used paper (including a base paper in a waste gypsum board therein), pulp residue, and sludge generated from a paper-making factory, and ones provided by treating them as activated charcoal can be used for the present invention, as similar to a general charcoal made from pine, oak, and Quecrus, charcoal made from bamboo, and activated charcoal.

The particle size of the organic carbide that is above-mentioned as an example is not limited in respect to the odor eliminating property of a building material for interiors obtained according to the present invention, and however, one of which the average particle diameter is within a range of 0.03 through 2 mm can be used in the following cases; for example, the case where such a problem as sense of beauty is provided that the tint in a cross-section of the building material for interiors becomes black, and the case where it is necessary to prevent dust at the time of fabricating the building material for interiors or at the time of cutting at a construction site.

A method of compounding the organic carbide is not limited particularly, and it may be added into a base material in powder-form or slurry-form, it may be previously mixed into an admixture to be contained in the building material for interiors and kneaded, and further it may be added to the inside of a base paper for gypsum board used as a surface material of the gypsum board.

The more the loading of the organic carbides is increased, the more the adsorption property of the obtained building material for interiors is improved, but the more the mechanical strength of the obtained the building material for interiors is reduced. Accordingly, the loading is appropriately 0.1 through 20 parts by weight, desirably 0.1 through 10 parts by weight, more desirably 0.1 through 7 parts by weight. In the case of less than 0.1 parts by weight, a significant difference is not recognized in odor eliminating property dependent on the presence or absence of the compounding of the organic carbide, and in the case of compounding over the above-mentioned range, the odor eliminating property is improved but the drop in physical properties such as mechanical strength is increased.

As an inorganic hygroscopic material used in the building material for interiors according to the present invention, all materials exhibiting hygroscopicity dependent on the presented environmental condition can be used. For example, clay minerals such as zeolites, diatomaceous earth (ex. Wakkanai diatomaceous shale), attapulgite, and monmorillonite (acid clay) are generally known, and any of them can be used for the present invention. Particularly, ones provided by calcining or acidizing them are known to exhibit more excellent hygroscopicity than non-treated ones and are particularly preferable. For example, activated clay provided by acidizing acid clay can be also used preferably. Of course, one or more kinds of the inorganic hygroscopic materials described above can be compounded so as to be used.

The method of compounding an inorganic hygroscopic material is not limited particularly, as it may be added into a base material in powder-form or slurry-form, may be previously mixed into an admixture to be contained in the building material for interiors and kneaded, and further may be added into inside of a surface material when the building material for interiors is composed by laminating the surface material.

The loading of the inorganic hygroscopic material is 3 through 60 parts by weight, preferably 5 through 20 parts by weight per 100 parts by weight of a base material. The more the loading of the inorganic hygroscopic material is increased, the more the hygroscopicity can be improved, but preference is not provided in the case of compounding over the above-mentioned range, since the strength of the building material for interiors is caused to drop. On the other hand, in the case of the loading less than 3 parts by weight, the appearance of a significant improvement in hygroscopicity of the building material for interiors cannot be achieved.

As a water repellent, all kinds that are publicly known can be used, and the inventors found that a silicone-based water repellent and/or a paraffinic water repellent provided below were appropriate, taking performance, price, and maturing time into account.

As a preferable silicone-based water repellent, specifically, for example, organosiloxanes disclosed in Japanese patent No. 2739872 and organopolysiloxanes disclosed in Japanese patent No. 2686792 can be provided.

As a preferable paraffinic water repellent, an emulsion provided by containing polyvinyl alcohol in an emulsion provided by emulsifying waxes with the melting point of 40 through 90° C. and olefin-maleic anhydride derivatives under basic condition in water, as disclosed in Japanese examined application publication No. 7-61889, can be provided.

As a method of compounding the water repellent into the building material for interiors having an odor eliminating property according to the present invention, not only addition into a base material or an admixture is made but also impregnation to hardened and molded one of the base materials to be obtained is made, and not limited to them.

The loading of the water repellent is not limited particularly but the amount capable of controlling the extension rate of the building material for interiors is allowed at the time of absorbing moisture, and for example, allowed is the amount capable of controlling the total water absorption rates of gypsum boards to be equal to or less than 10% at dipping in water for 2 hours (JIS A 6901 application) or the extension rates to be equal to or less than 0.1% at absorbing water for 2 hours. The loading can be 0.05 through 1 parts by weight, preferably 0.3 through 0.7 parts by weight, per 100 parts by weight of a base material for a silicone-based water repellent, and the loading can be 0.5 through 5 parts by weight, preferably 2 through 4 parts by weight, per 100 parts by weight of a base material for a paraffinic water repellent.

Regarding the amount of the water repellents, as the loading is increased, the total water absorption rate for 2 hours and the extension rate at the time of absorbing water for 2 hours described above can be reduced, and water repellency and size stability become good, but in the case of compounding over the above-mentioned range, the costs for the material relative to the effect becomes so high to be inferior in respect to economy. On the other hand, for any water repellents, when the loading is too small, the desired water repellency and size stability cannot be obtained.

Next, adding and compounding the components described above into the building material for interiors having an odor eliminating property according to the present invention will be explained.

Any building material for interiors having an odor eliminating property can be produced in the ordinary fabrication line as described above.

For example, a board-shaped gypsum board having an odor eliminating property can be produced in the ordinary gypsum-board fabrication line. In the fabrication liner the hydrazide compound is compounded into one or both of calcined gypsum and a commonly used admixture, and/or a gypsum board having an odor eliminating property involved in the scope of the present invention can be fabricated using a base paper for gypsum board in which the compound is added inside. Similarly, a gypsum board with an odor eliminating property having high hygroscopcity and/or size stability can be obtained by compounding the carbide, the inorganic hygroscopic material, and/or the water repellent in accordance with the above method.

Each kind of cement plate can be also produced in the ordinary fabrication line by means of compression molding, extrusion molding, and sheet-making after addition of water and kneading. Then, similar to the case of the gypsum board, each kind of cement plate having the desired odor eliminating property can be obtained by compounding the component such as the hydrazide compound into one or both of a raw material of cement and a commonly used admixture.

Also, even when a powder-form or pasty gypsum plaster, a gypsum-based putty, a gypsum-based jointing material, a cement mortar, and a dolomite plaster are fabricated as the building material for interiors according to the present invention, the fabrication can be made in an ordinary fabrication facility for each building material, and the substance as described above can be appropriately compounded similar to the case of the board-shaped building material for interiors.

Additionally, it goes without saying that in the fabrication line for the above-mentioned board-shaped, powder-form, or pasty building material for interiors, a publicly-known admixture such as a pulp fiber or a glass fiber, a publicly-known foaming agent, a setting modifier, or a adhesion enhancement agent as well as a base material such as a gypsum and a cement and the above-mentioned hydrazide compound, etc. can be compounded appropriately.

In such an ordinary fabrication line, as a building material for interiors according to the present invention, any of eight kinds of variations as follows can be produced freely:

(1) A building material for interiors having an odor eliminating property in which only a hydrazide compound is compounded.

(2) A building material for interiors having an odor eliminating property in which a hydrazide compound and an organic carbide are compounded, (3) A building material for interiors having an odor eliminating property in which a hydrazide compound and an inorganic hygroscopic material are compounded, (4) A building material for interiors having an odor eliminating property in which a hydrazide compound and a water repellent are compounded, (5) A building material for interiors having an odor eliminating property in which a hydrazide compound, an inorganic hygroscopic material, and a water repellent are compounded, (6) A building material for interiors having an odor eliminating property in which a hydrazide compound, an organic carbide, and a water repellent are compounded, (7) A building material for interiors having an odor eliminating property in which a hydrazide compound, an organic carbide, and an inorganic hygroscopic material are compounded, and (8) A building material for interiors having an odor eliminating property in which a hydrazide compound, an organic carbide, an inorganic hygroscopic material, and a water repellent are compounded.

Next, an interior structure of a building containing the building material for interiors according to the present invention will be explained.

Generally, in new construction work, refurbishing, and reconstruction work of buildings, a building material for interiors has been used in large quantity as a substrate material for interiors, a surface finishing material, or a material for composing floor substrates, on a part of the interior structure, that is, an inner surface of an external wall, both surfaces of a partition wall, and a surface of a ceiling. For example, a gypsum board is laminated in combination with one or more another kinds of boards directly or indirectly by a jig, and set to a skeleton and a structural member for forming the surface for interiors. Also, a gypsum plaster is applied on an application surface of substrate of a lath board. Additionally, an adhesive for interiors (ex. GL Bond (trade name) produced by Yoshino Gypsum Co., Ltd.) is heaped up in the shape of dumplings to a wall of the skeleton in order to set and fix the gypsum board to the skeleton. Putty for interiors and jointing material are used for jointing and unevenness-adjusting on a constructed surface of the gypsum board that is set up like that.

The building material for interiors having an odor eliminating property according to the present invention can be used for such use without exception, and can be contained in a part of the above-mentioned interior structure.

Specifically, when the building material for interiors having an odor eliminating property according to the present invention is a gypsum board having an odor eliminating property, such excellent odor eliminating effect can be obtained that aldehydes generated not only on a front surface for interiors but also on a back surface are captured for certain by lamination in combination with one or more another kinds of building materials and setting up to a skeleton or a structural member for forming the surfaces for interiors on a wall, a ceiling, and a floor, directly or indirectly by a jig according to the conventional construction method.

Even when the building material for interiors having an odor eliminating property according to the present invention is a hygroscopic gypsum plaster, the plaster is applied similar to a conventional one, and if the applied substrate as well as the applied surface at the front surface side is a face plate having air permeability such as a gypsum board, aldehydes generated from the gypsum board at the back surface side can be effectively captured. Moreover, when the building material for interiors having an odor eliminating property according to the present invention is putty for interiors or jointing material that have odor eliminating properties, the excellent effect of capturing aldehydes is provided at the place of construction with them and the effect of eliminating odor can be obtained.

A building material for interiors having an odor eliminating property according to the present invention can be used not only for a part of an interior structure in new construction work for a building, but also for an interior structure that can be an object of construction in refurbishing or reconstruction work for an existing interior structure.

Particularly, in the building material for interiors according to the present invention, board-shaped with a thin board-thickness and powder-form or pasty and capable of being thinly applied are preferred to apply the building material for interiors according to the present invention directly on the surface without scrapping an existing interior structure. For example, gypsum board and slate, which contain glass fiber cloth, shown as examples, are suitable for use in such a modification work. As for the thickness of the board, approximately 3 through 10 mm is proper, and the specific gravity thereof is equal to or more than approximately 0.5, and an interior structure after modification excellent in odor eliminating property as well as surface hardness, fire resistance, and sound insulation can be obtained.

Herein, the existing interior structure described above is not limited particularly as long as it is an interior structure, and walls such as a partition wall and a party wall, a floor structure constructed on a ceiling and a common floor joist, and a floor such as a double floor, a floating floor, a poured floor, and a free access floor are suitable. Also, a structure around steps and a backing of a unit bath may be included.

A surface material constituting the existing interior structure is not particularly limited in the present invention, and as for a wall, ones provided by applying paint-finishing, wallpaper or cloth finishing, and fiber wall finishing, mainly on a constructed surface of a general gypsum board or hard wood chip cement board are shown as examples, and as for a ceiling, a surface of a ceiling composed by a gypsum board for acoustic absorption, a decoration gypsum board, a calcium silicate board, or a rock wool-board as well as a system ceiling are shown as examples. Additionally, as for a floor, each kind of flooring, each kind of parquet floor, and a tatami floor are shown as examples. Herein, when a carpet and a tatami are laid, it is desirable to implement the present invention after they are removed.

Also, the modification method is not particularly limited, and the methods as follows can be shown as examples.

(1) The surface of an existing interior structure is checked, and if an obstruction is generated when the building material according to the present invention is applied to an unevenness of the surface, the place is adjusted according to need. At that time, there is no necessity to remove a finishing agent on the surface of an existing interior structure.

(2) Then, the building material according to the present invention is applied and fixed on a surface of the existing interior structure. Then, as a fixing method, not only a commonly performed fixing method employing a nail, a machine screw, and a tucker but also these fasteners and an adhesive may be used in combination. Also, it is possible to apply and fix by using only an adhesive.

(3) A head of a nail or machine screw on the surface of the building material for interiors according to the present invention applied as described above, and a joint of the building material are treated. In the case of fixing with only an adhesive, only the joints are to be treated.

(4) After drying of the jointing material is checked, the surface of the building material for interiors is finished by the commonly performed method employing a commonly used a finishing agent, for example, paint, a cloth, or wallpaper.

Additionally, it goes without saying that the use of the building material for interiors having an odor eliminating property according to the present invention is not limited to the interior structure as described above, and the concentration of contamination with VOC in indoor space is also reduced by placing a bibelot, a monument, or a decoration of which a part or all are formed using the building material in interiors, so as to being useful for odor elimination.

Next, the present invention is further specifically illustrated with reference to examples and comparisons.

As one example of the building material for interiors having an odor eliminating property according to the present invention, a gypsum board having an odor eliminating property was selected so as to perform the tests. Then, since respective base papers for the gypsum board on the front and back surfaces of the gypsum board having an odor eliminating property had approximately the same gas permeability, tests of the odor eliminating property were performed on only one surface of the gypsum board. Additionally, the present invention is not limited to it, and similar effect can be also obtained in regard to building materials for interiors having an odor eliminating property such as gypsum plaster and gypsum putty that have an odor eliminating property.

[Test of Odor Eliminating Property Against Formaldehyde]

The samples for test were fabricated by applying a polyvinyl chrolide board with approximately same sizes on the back surface of a gypsum board using aluminum tape. Then, After the 8 samples for test (with effective area of 12.96 $m^2$) were applied to a wall surface for interiors, to which the polyvinyl chloride boards faced, in the test room in accordance with the following specification and set so that a new wall surface for interiors was formed by the gypsum board, gaps around the door of the test room were sealed with aluminum tape so that the test room was in closed state.

Formaldehyde gas with high concentration was injected into the test room so that the initial concentration of formaldehyde in room air was 5 ppm, and then, the room air was sampled at every certain time interval and the variation of the formaldehyde concentration in the room air with time was measured, by using the gas sampling vessel and the detection tube No. 91 in series made by GASTEC CO., Ltd.

The measurements were continuously performed for 30 hours, and when the formaldehyde concentration could not be detected in the room air within the time interval, the test was finished at that time.

Additionally, the temperature and relative humidity in the test room were maintained at 25° C. and 70% RH during the test, respectively.

[Specification of Test Room]

A prefabricated house, 3 floor space in tsubo-type.

The intenalt volume is 29 $m^3$, 2.7 m×3.6 m×3 m (height) (that corresponds to the 6 tatamis' area.)

[Test of Formaldehyde Gas Releasing]

After the test of the odor eliminating property described above had been finished, the temperature and the relative humidity in the room were adjusted to 40° C. and 60% RH respectively, and the conditions were maintained, and subsequently, the formaldehyde concentration in the room air was measured, so as to confirm the release of formaldehyde gas from the gypsum board with an odor eliminating property.

Additionally, in the test of odor eliminating property, if formaldehyde was detected in the test room even when 30 hours had passed since the start of the test, the tape for sealing the gaps around the door was removed, the door was opened, the residual formaldehyde gas purged from the room, sealing was made in a similar way again, adjustment and maintenance to the above-mentioned temperature (40° C.) and relative humidity (60% RH) were made, and the variation of the formaldehyde concentration in the room with time was measured, so as to confirm the release of formaldehyde gas from the gypsum board with an odor eliminating property.

[Test of Odor Eliminating Property Against Toluene Gas]

In a test room similar to the test room used for the test of the odor eliminating property against formaldehyde gas, the 8 samples for test were applied, and the temperature and humidity conditions similar to the test of odor eliminating property against formaldehyde gas were provided. Then, volatile gas that is collected from toluene at ordinary temperature was injected in the room, the initial concentration of toluene gas in room air was 5 ppm, the room air was sampled at every certain time interval and the variation of the toluene gas concentration in the room air with time was measured, by using the gas sampling vessel and the detection tube No. 122 in series made by GASTEC CO., Ltd. Herein, the lower limit of measurement by the detection tube was 1 ppm.

After confirming that every measured value has reached equilibrium, the temperature and humidity in the room were changed to 40° C. and 60% RH similar to the test for the release of formaldehyde gas, and the measure for the release of toluene gas was performed using the detection tube.

[Measurement of Total Amount of Water Absorption and the Extension Rate at that Time]

The total amount of water absorption was measured by dipping 3 test pieces of 30 cm square in water at 20±3° C. for 2 hours according to the item of JIS A 6901 sheathing gypsum board GB-S. Also, at that time, the extension rate at the time of absorbing water for 2 hours was measured by fixing a dial gage in one side support and in the longitudinal and transverse directions of the test piece. The average of the 3 obtained measured values is referred to as the measurement result.

[Measurement Method of the Amount of Moisture Absorption and Release]

3 test pieces of 30 cm square were dried at the constant temperature of 40° C. to be for the measurement of the amount of moisture absorption and release, and then, all except the front surface of the test piece were sealed with aluminum tape so that moisture was absorbed and released only from the front surface of the test piece, and after the seal-treated test piece was left at rest in a thermo-hygrostat at a room temperature of 25° C. and a relative humidity of 50% RH for 24 hours, the amount of moisture absorption was measured by leaving at rest in the thermo-hygrostat at a room temperature of 25° C. and a relative humidity of 90% RH for 24 hours. Then, the amount of moisture release was measured by further leaving the test piece at rest in the thermo-hygrostat at the room temperature of 25° C. and the relative humidity of 50% RH for 24 hours. The average of the 3 obtained measured values is referred to as the measurement result.

[Used Hydrazide Compound, Organic Carbide, Hygroscopic Material, and Water Repellent]

In fabricating the gypsum board used for the examples and comparisons, adipodihydrazide (the trade name "CHEMCATCH" made by Otsuka Chemical Co., Ltd.) was employed as the hydrazide compound, and activated carbon powder made by Kanto Kagaku Co., Ltd. was employed as the organic carbide. Also, activated clay (trade name "Nikkaraito G-36" made by Nippon Kassei Hakudo Co., Ltd.) was employed as the inorganic hygroscopic material. Furthermore, methylhydrogenpolysiloxane (trade name "KF-99" made by Shin-Etsu Chemical Co., Ltd.) being a silicone-based water repellent was employed as the water repellent.

EXAMPLE 1

A gypsum board with an odor eliminating property was fabricated by compounding 1.0 part by weight of adipodihydrazide as the hydrazide compound per 100 parts by weight of gypsum according to an ordinary method in ordinary gypsum board fabrication lines. Then, in respect of the obtained gypsum board with an odor eliminating property (the thickness of 12.5 mm, the width of 910 mm, and the specific gravity of 0.7), the measurements were performed in respect of respective items of the tests described above. Respective measurement results for the amount of water absorption for 2 hours, the extension rate, and the amount of moisture absorption and release is are shown in the following Table 1.

TABLE 1

|  |  | Adipodihydrazide (parts by weight) | Activated clay (parts by weight) | Methylhydrogen polysiloxane (parts by weight) |
|---|---|---|---|---|
| Examples | 1 | 1.0 | 0 | 0 |
|  | 2 | 0.5 | 10 | 0.3 |
|  | 3 | 1.0 | 10 | 0.3 |
|  | 4 | 1.0 | 20 | 0.3 |
|  | 5 | 1.0 | 20 | 0 |
| Comparisons | 1 | 0 | 0 | 0 |
|  | 2 | 0 | 5 | 0.3 |
|  | 3 | 0 | 20 | 0.3 |

|  |  | Amount of water absorption (%) | Extension rate (%) | | Amount of moisture absorption ($g/m^2$) | Amount of moisture release ($g/m^2$) |
|---|---|---|---|---|---|---|
|  |  |  | Longi-tudinal | Trans-verse |  |  |
| Examples | 1 | 58.0 | 0.02 | 0.03 | 62 | 62 |
|  | 2 | 24.0 | 0.06 | 0.08 | 194 | 197 |
|  | 3 | 24.6 | 0.05 | 0.07 | 196 | 200 |
|  | 4 | 24.6 | 0.06 | 0.08 | 311 | 314 |
|  | 5 | 60.5 | 0.18 | 0.24 | 320 | 321 |
| Comparisons | 1 | 58.6 | 0.02 | 0.03 | 62 | 63 |
|  | 2 | 25.8 | 0.04 | 0.06 | 128 | 128 |
|  | 3 | 25.0 | 0.06 | 0.08 | 306 | 310 |

Figure 2:
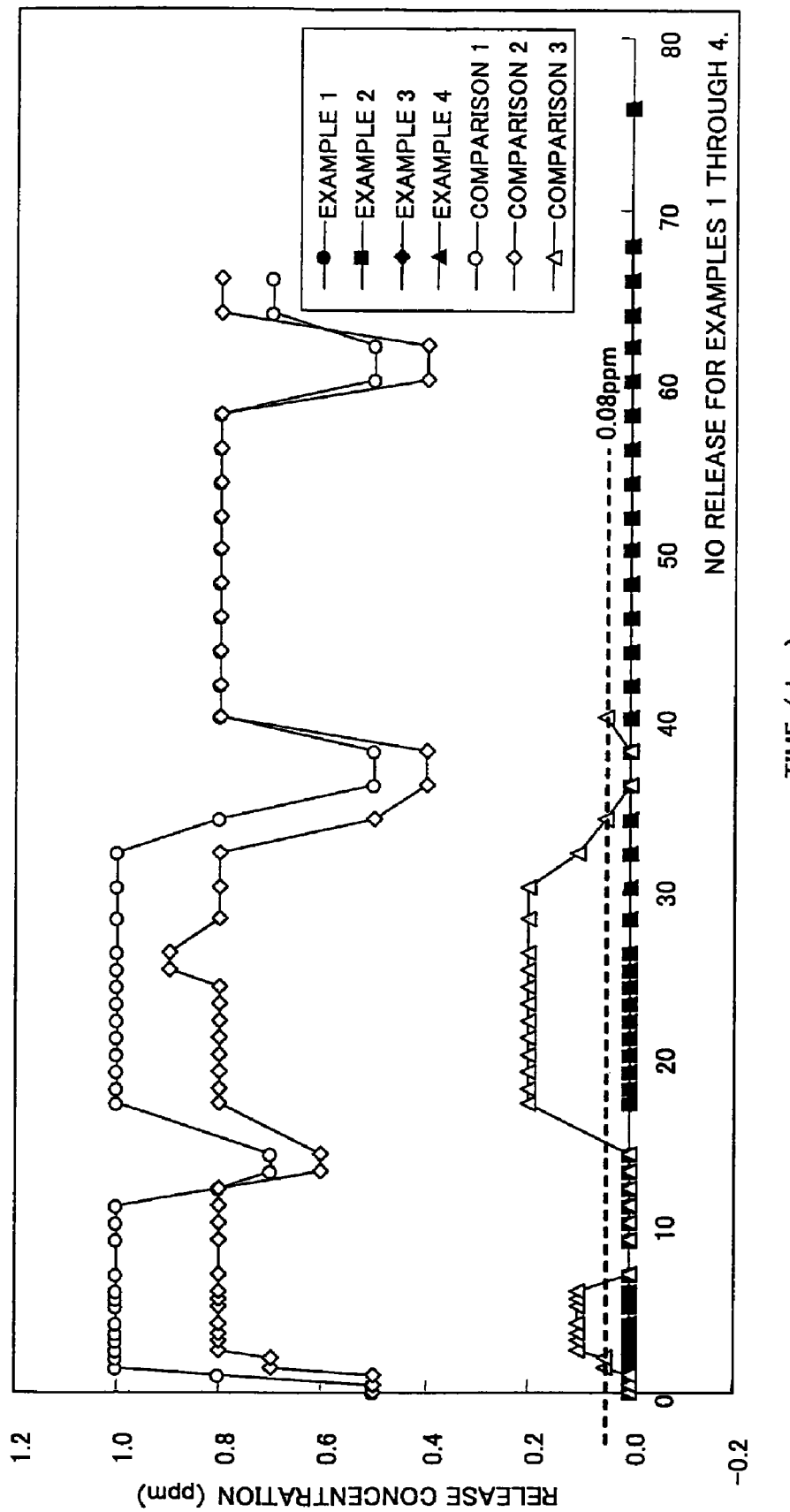
FIG. 2 is a graph of plotting the results of a test of releasing formaldehyde gas.

The measured values for the test of odor eliminating property against formaldehyde gas and the test for the release are plotted in FIGS. 1 and 2, respectively, wherein the horizontal axis indicates elapsed time from the start of the test and the vertical axis indicates the formaldehyde concentration (ppm) in the room air at the elapsed time.

EXAMPLE 2

A gypsum board with an odor eliminating property (the thickness of 12.5 mm, the width of 910 mm, and the specific gravity of 0.7) in which 0.5 parts by weight of adipodihydrazide as the hydrazide compound, 10 parts by weight of activated clay as the inorganic hydroscopic material, and 0.3 parts by weight of methylhydrogenpolysiloxane being a silicone-based one as the water repellent were compounded into 100 parts by weight of gypsum respectively was fabricated according to an ordinary method. Then, in respect of the obtained gypsum board with an odor eliminating property, the respective measurements were performed in respect of respective items of the tests described above. The respective measurement results are shown in Table 1, FIGS. 1 and 2 similar to Example 1.

EXAMPLE 3

In the compounding condition of Example 2, only the change to 1.0 part by weight of adipodihydrazide per 100 parts by weight of gypsum was made and others were similar to Example 2 so as to fabricate a gypsum board with an odor eliminating property, the thickness of 12.5 mm the width of 910 mm, and the specific gravity of 0.7 according to an ordinary method. Then, in respect of the obtained gypsum board with an odor eliminating property, the respective measurements were performed in respect of respective items of the tests described above. The respective measurement results are shown in Table 1, FIGS. 1 and 2 similar to Example 1.

EXAMPLE 4

In the compounding condition of Example 2, the changes to 1.0 part by weight of adipodihydrazide and 20 parts by weight of activated clay per 100 parts by weight of gypsum was made and others were similar to Example 2 so as to fabricate a gypsum board with an odor eliminating property, the thickness of 12.5 mm, the width of 910 mm, and the specific gravity of 0.7 according to an ordinary method. Then, in respect of the obtained gypsum board with an odor eliminating property, the respective measurements were performed in respect of respective items of the tests described above. The respective measurement results are shown in Table 1, FIGS. 1 and 2 similar to Example 1.

EXAMPLE 5

In the compounding condition of Example 3, the changes to 20 parts by weight of activated clay and no loading of methylhydrogenpolysiloxane per 100 parts by weight of gypsum was made and others were similar to Example 3 so as to fabricate a gypsum board with an odor eliminating property, the thickness of 12.5 mm, the width of 910 mm, and the specific gravity of 0.7 according to an ordinary method. Then, in respect of the obtained gypsum board with an odor eliminating property, the respective measurements were performed in respect of respective items of the tests described above except the test of odor eliminating property and the test for the release. The respective measurement results are shown in Table 1, similar to Example 1.

EXAMPLE 6

In respect of the gypsum board with an odor eliminating property (the thickness of 12.5 mm, the width of 910 mm, and the specific gravity of 0.7) (shown in the following Table 2), the measurement for odor eliminating property against toluene gas was performed.

TABLE 2

|  |  | Adipodihydrazide (pats by weight) | Activated clay (parts by weight) | Methyl hydrogen polysiloxane (parts by weight) | Activated carbon powder (parts by weight) |
|---|---|---|---|---|---|
| Examples | 6 | 1.0 | 0 | 0 | 0 |
|  | 7 | 1.0 | 0 | 0 | 5 |

TABLE 2-continued

| | Adipodihydrazide (pats by weight) | Activated clay (parts by weight) | Methyl hydrogen polysiloxane (parts by weight) | Activated carbon powder (parts by weight) |
|---|---|---|---|---|
| 8 | 1.0 | 10 | 0.3 | 10 |
| 9 | 0 | 0 | 0 | 10 |

Figure 3:
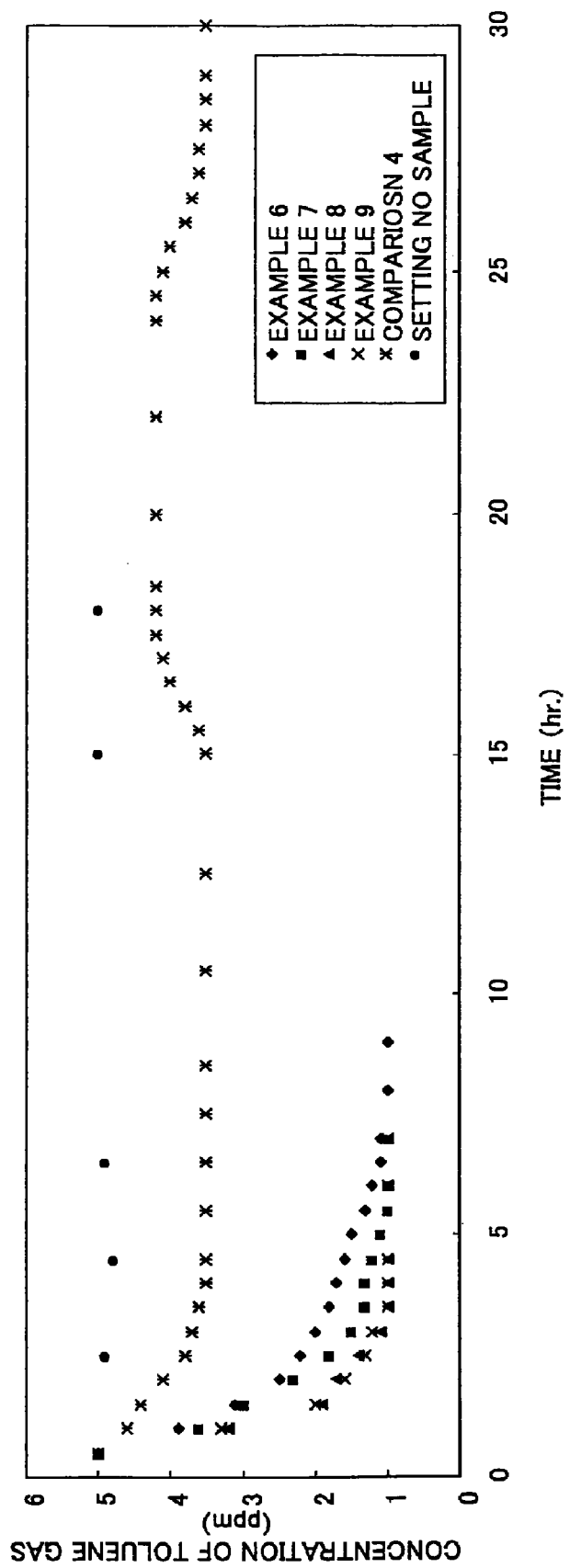
FIG. 3 is a graph of plotting the results of a test of an odor eliminating property against toluene gas.

The measured values for the test of odor eliminating property against toluene gas are plotted in FIG. 3, wherein the horizontal axis indicates elapsed time from the start of the test and the vertical axis indicates the toluene gas concentration (ppm) in the room air at the elapsed time.

EXAMPLE 7

5 parts by weight of activated carbon powder as the organic carbide per 100 parts by weight of gypsum was compounded (Table 2) other than the compounding condition of Example 1, so as to fabricate a gypsum board with an odor eliminating property according to an ordinary method. Then, in respect of the obtained gypsum board with an odor eliminating property (the thickness of 12.5 mm, the width of 910 mm, and the specific gravity of 0.7), the measurements similar to Example 6 were performed. The measured values for the test of odor eliminating property are plotted respectively in FIG. 3, similar to Example 6.

EXAMPLE 8

In addition to the compounding condition of Example 3, 10 parts by weight of activated carbon powder per 100 parts by weight of gypsum was further compounded (Table 2) so as to fabricate a gypsum board with an odor eliminating property, the thickness of 12.5 mm, the width of 910 mm, and the specific gravity of 0.7, according to an ordinary method. Then, in respect of the obtained gypsum board with an odor eliminating property, the measurements similar to Example 6 were performed. The measured values for the test of odor eliminating property are plotted respectively in FIG. 3, similar to Example 6.

EXAMPLE 9

10 parts by weight of activated carbon powder per 100 parts by weight of gypsum was compounded (Table 2) other than the compounding condition of Example 1, so as to fabricate a gypsum board with an odor eliminating property, the thickness of 12.5 mm, the width of 910 mm, and the specific gravity of 0.7. Then, in respect of the obtained gypsum board with an odor eliminating property, the measurements similar to Example 6 were performed. The measured values for the test of odor eliminating property are plotted respectively in FIG. 3, similar to Example 6.

{Comparison 1}

A gypsum board (with the thickness of 12.5 mm, the width of 910 mm, and the specific gravity of 0.7) was fabricated according to an ordinary method in ordinary gypsum board fabrication line, without compounding adipodihydrazide, activated carbon powder, activated clay, and methylhydrogenpolysiloxane. Then, in respect of the obtained gypsum board, the respective measurements were performed in respect of respective items of the tests described above. The respective measurement results are shown in Table 1, FIGS. 1 and 2 similar to Example 1.

{Comparison 2}

A gypsum board (with the thickness of 12.5 mm, the width of 910 mm, and the specific gravity of 0.7) was fabricated by compounding 5 parts by weight of activated clay and 0.3 parts by weight of methylhydrogenpolysiloxane without compounding adipodihydrazide, per 100 parts by weight of gypsum according to an ordinary method. Then, in respect of the obtained gypsum board, the respective measurements were performed in respect of respective items of the tests described above. The respective measurement results are shown in Table 1, FIGS. 1 and 2 similar to Example 1.

{Comparison 3}

In the compounding condition of Comparison 2, only the compounding change to 20 parts by weight of activated clay was made and others were similar to Comparison 2 so as to fabricate a gypsum board (with the thickness of 12.5 mm, the width of 910 mm, and the specific gravity of 0.7) according to an ordinary method. Then, in respect of the obtained gypsum board with an odor eliminating property, the respective measurements were performed in respect of respective items of the tests described above. The respective measurement results are shown in Table 1, FIGS. 1 and 2 similar to Example 1.

{Comparison 4}

The measurement similar to Example 6 was performed using the gypsum board with an odor eliminating property in Comparison 1. The results of the test of odor eliminating property against toluene gas are plotted in FIG. 3 similar to Example 6.

Also, in respect of the test of odor eliminating property against formaldehyde, it was confirmed that the gaps around the door of the test room were in perfectly sealed condition according to the above-mentioned method, formaldehyde etc. was absorbed and released from the surface of the inner wall, and formaldehyde concentration in the room air was maintained at initial 5 ppm for at least 25 hours after the start of the experiment when the sample was not set. The measurement results are plotted in FIG. 1 (setting no sample).

Similarly, in the test of odor eliminating property against toluene gas, it was also confirmed that sealing of the test room was perfect and toluene gas concentration in the room air was maintained at initial 5 ppm for at least 15 hours after the start of the experiment when the sample was not set. The measurement results are plotted in FIG. 3 (setting no sample).

From the result of the test of odor eliminating property against formaldehyde gas in FIG. 1 and the result of the test of releasing formaldehyde in FIG. 2, by compounding adipodihydrazide as the hydrazide compound into the gypsum, aldehydes were captured on the one surface of the gypsum board, so that the formaldehyde concentration in the room was not detected after approximately 9 hours had passed at latest. Since permeability of the base papers for gypsum board on the front and back surfaces is nearly equal, it is easily thought that when formaldehyde is captured on both surfaces of the gypsum board, the formaldehyde concentration in the room becomes not detectable in a shorter time.

Also, from the result of the test for the release in FIG. 2, while it was confirmed that the gypsum board without compounding adipodihydrazide released formaldehyde and the release could be somewhat controlled by compounding the inorganic hygroscopic material, the release of formaldehyde to indoors was not detected at all and it was found to have an excellent odor eliminating property without release in regard of the gypsum board having an odor eliminating property according to the present invention in which adipodihydrazide was compounded.

Furthermore, from the result of the test of odor eliminating property against toluene gas in FIG. 3, whereas the captured quantity of toluene gas was small and the toluene gas captured at once was released dependent on a change in the temperature and humidity conditions in the test room for the gypsum board in Comparison 4 (or 1) that does not contain the hydrazide compound, the organic carbide, etc. according to the present invention at all, the indoor concentration decreased to be equal to or less than the limit of the measurement of the detection tube in a comparatively short time from the start of the measurement and release of toluene gas over the detection limit was not found to be dependent on a change in temperature and humidity conditions in the room.

Also, it is obvious that the gypsum board in which the organic carbide was further compounded captured toluene gas for a shorter time than the gypsum board in which only the hydrazide compound was compounded.

Additionally, the hydrazide compound and the organic carbide have no harmful effect on each other and fully exhibit respective abilities. Thus, every VOC can be captured effectively by applying the building material for interiors in the room in which the some kinds of VOCs are filled. Moreover, after such building material for interiors is applied, if new VOC are generated, the new VOC can be also captured effectively.

As illustrated above, according to the present invention, a building material for interiors, excellent in convenience, thermal insulation property, and economy, having much capacity for moisture absorption and release, also having high size stability at the time of moisture absorption and release, and having an excellent odor eliminating property such that VOCs generated indoors, especially formaldehyde being a representative material of them and acetaldehyde originating from smoking and toluene, are effectively captured and are not released, can be obtained. Then, hygroscopicity and an odor eliminating property can be selectively provided to a building material for interiors by appropriately selecting and compounding the agents according to the present invention or by changing the loading of them.

Also, an interior structure of a building that can reduce VOC concentration without ventilation is obtained by employing the building material for interiors.

Additionally, it goes without saying that the present invention is not limited to the examples, but various modifications and variations can be provided within the scope of the present invention.

The invention claimed is:

1. A method of modifying an interior structure of an existing building comprising:
    applying a gypsum board on a surface of the interior structure,
    the gypsum board comprising a gypsum core containing a gypsum and a base paper for gypsum board covering the gypsum core,
    the base paper for gypsum board being a base paper for gypsum board having air permeability,
    at least one kind of hydrazide compound being compounded in at least one of the gypsum core and the base paper for gypsum board,
    a molecule of the at least one kind of hydrazide compound having at least one hydrazide group, and
    a content of the at least one kind of hydrazide compound being 0.01 part by weight or more and 10 parts by weight or less per 100 parts by weight of the gypsum.

* * * * *